United States Patent
Fan et al.

(10) Patent No.: US 11,419,566 B2
(45) Date of Patent: Aug. 23, 2022

(54) SYSTEMS AND METHODS FOR IMPROVING IMAGE QUALITY WITH THREE-DIMENSIONAL SCOUT

(71) Applicant: General Electric Company, Schenectady, NY (US)

(72) Inventors: Jiahua Fan, New Berlin, WI (US); Yannan Jin, Niskayuna, NY (US); Dominic Crotty, Waukesha, WI (US); John Moore Boudry, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 695 days.

(21) Appl. No.: 15/813,030

(22) Filed: Nov. 14, 2017

(65) Prior Publication Data

US 2019/0142357 A1    May 16, 2019

(51) Int. Cl.
| | | |
|---|---|---|
| *A61B 6/00* | (2006.01) | |
| *A61B 6/03* | (2006.01) | |
| *A61B 6/04* | (2006.01) | |

(52) U.S. Cl.
CPC ............ *A61B 6/5205* (2013.01); *A61B 6/032* (2013.01); *A61B 6/4035* (2013.01); *A61B 6/4435* (2013.01); *A61B 6/481* (2013.01); *A61B 6/482* (2013.01); *A61B 6/488* (2013.01); *A61B 6/50* (2013.01); *A61B 6/542* (2013.01); *A61B 6/545* (2013.01); *A61B 6/0407* (2013.01); *A61B 6/405* (2013.01); *A61B 6/4241* (2013.01); *A61B 6/563* (2013.01)

(58) Field of Classification Search
None
See application file for complete search history.

(56) References Cited

U.S. PATENT DOCUMENTS

| | | | | |
|---|---|---|---|---|
| 5,970,112 A | * | 10/1999 | Hsieh | G21K 1/04 378/8 |
| 8,811,709 B2 | | 8/2014 | Wu et al. | |
| 2003/0031299 A1 | * | 2/2003 | Ohishi | A61B 6/481 378/162 |
| 2006/0159223 A1 | * | 7/2006 | Wu | A61B 6/032 378/18 |
| 2008/0253635 A1 | * | 10/2008 | Spies | G06T 11/008 382/131 |
| 2009/0122952 A1 | * | 5/2009 | Nishide | A61B 6/542 378/4 |
| 2015/0359501 A1 | * | 12/2015 | Eronen | A61B 6/032 378/62 |
| 2015/0366525 A1 | * | 12/2015 | Sandholm | A61B 6/5217 378/4 |
| 2016/0242712 A1 | * | 8/2016 | Jin | A61B 6/488 |
| 2016/0324499 A1 | * | 11/2016 | Sen Sharma | A61B 6/032 |
| 2017/0340304 A1 | * | 11/2017 | Qiulin | A61B 6/5205 |
| 2018/0365869 A1 | * | 12/2018 | Ruijters | A61B 6/032 |
| 2019/0066345 A1 | * | 2/2019 | Peng | G06T 11/008 |

* cited by examiner

*Primary Examiner* — Yi-Shan Yang

(57) ABSTRACT

Methods and systems are provided for improving image quality with three-dimensional (3D) scout scans for computed tomography (CT) imaging. In one embodiment, a method comprises reconstructing an image from projection data acquired during a diagnostic scan of a patient with corrections based on scout projection data acquired during a 3D scout scan of the patient. In this way, the image quality of a diagnostic image can be improved by using 3D scout data to correct projection data or image data.

5 Claims, 6 Drawing Sheets

SYSTEMS AND METHODS FOR IMPROVING IMAGE QUALITY WITH THREE-DIMENSIONAL SCOUT

FIELD

Embodiments of the subject matter disclosed herein relate to non-invasive diagnostic imaging, and more particularly, to three-dimensional scout scans for computed tomography (CT) imaging.

BACKGROUND

Non-invasive imaging technologies allow images of the internal structures or features of a patient to be obtained without performing an invasive procedure on the patient. In particular, such non-invasive imaging technologies rely on various physical principles, such as the differential transmission of x-rays through the target volume or the reflection of acoustic waves, to acquire data and to construct images or otherwise represent the observed internal features of a patient.

For example, in CT and other x-ray based imaging technologies, x-ray radiation spans a subject of interest, such as a human patient, and a portion of the radiation impacts a detector where the image data is collected. In digital x-ray systems a photodetector produces signals representative of the amount or intensity of radiation impacting discrete pixel regions of a detector surface. The signals may then be processed to generate an image that may be displayed for review. In CT systems a detector array including a plurality of detector elements produces similar signals through various positions as a gantry is displaced around a patient.

Typically, to plan an optimal diagnostic scan, a patient undergoes a scout scan. A scout scan is conventionally a two-dimensional (2D) scan of the patient that produces 2D scout projection data. A 2D image reconstructed from the 2D scout projection data can be used to determine and confirm the general location of particular anatomy or another region of interest prior to performing the full diagnostic scan.

BRIEF DESCRIPTION

In one embodiment, a method comprises reconstructing an image from projection data acquired during a diagnostic scan of a patient with corrections based on scout projection data acquired during a three-dimensional (3D) scout scan of the patient. In this way, the image quality of a diagnostic image can be improved by using 3D scout data to correct projection data or image data.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
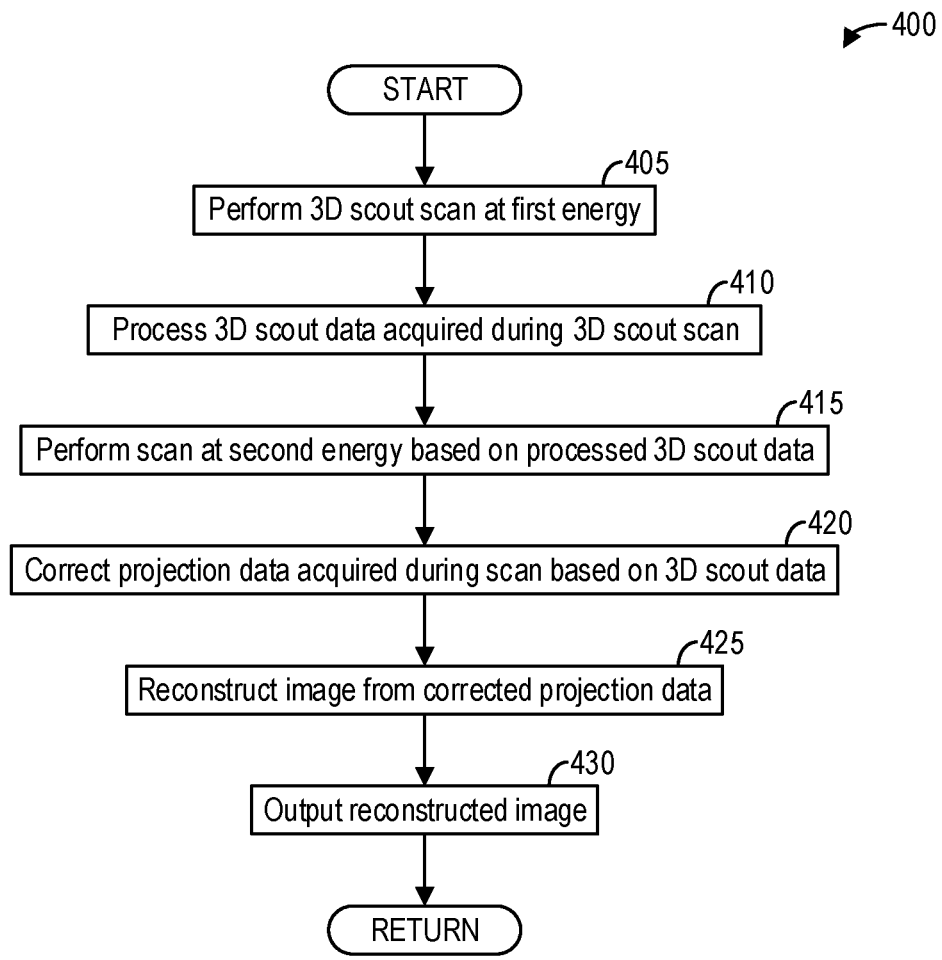
FIG. 4 shows a high-level flow chart illustrating an example method for correcting projection data with 3D scout data acquired at a different energy according to an embodiment.
Figure 5:
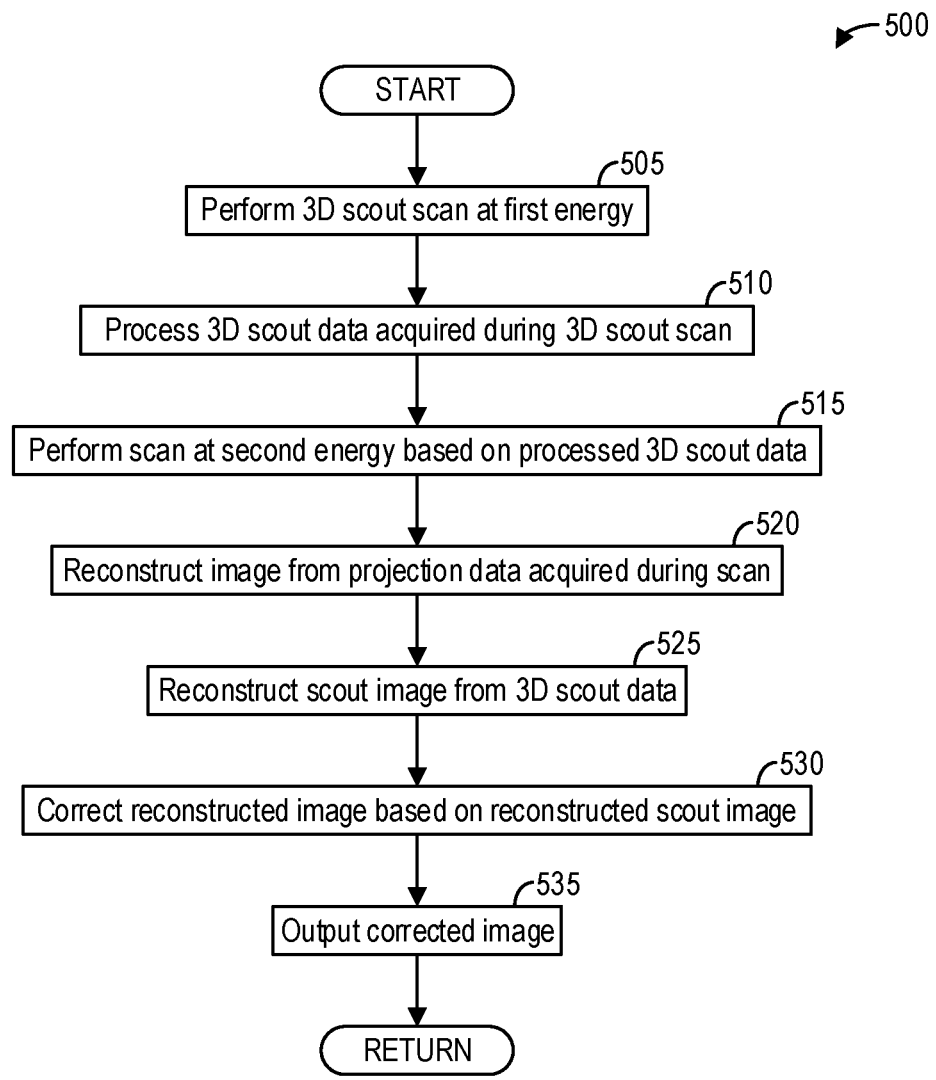
FIG. 5 shows a high-level flow chart illustrating an example method for correcting image data with 3D scout data acquired at a different energy according to an embodiment.
Figure 6:
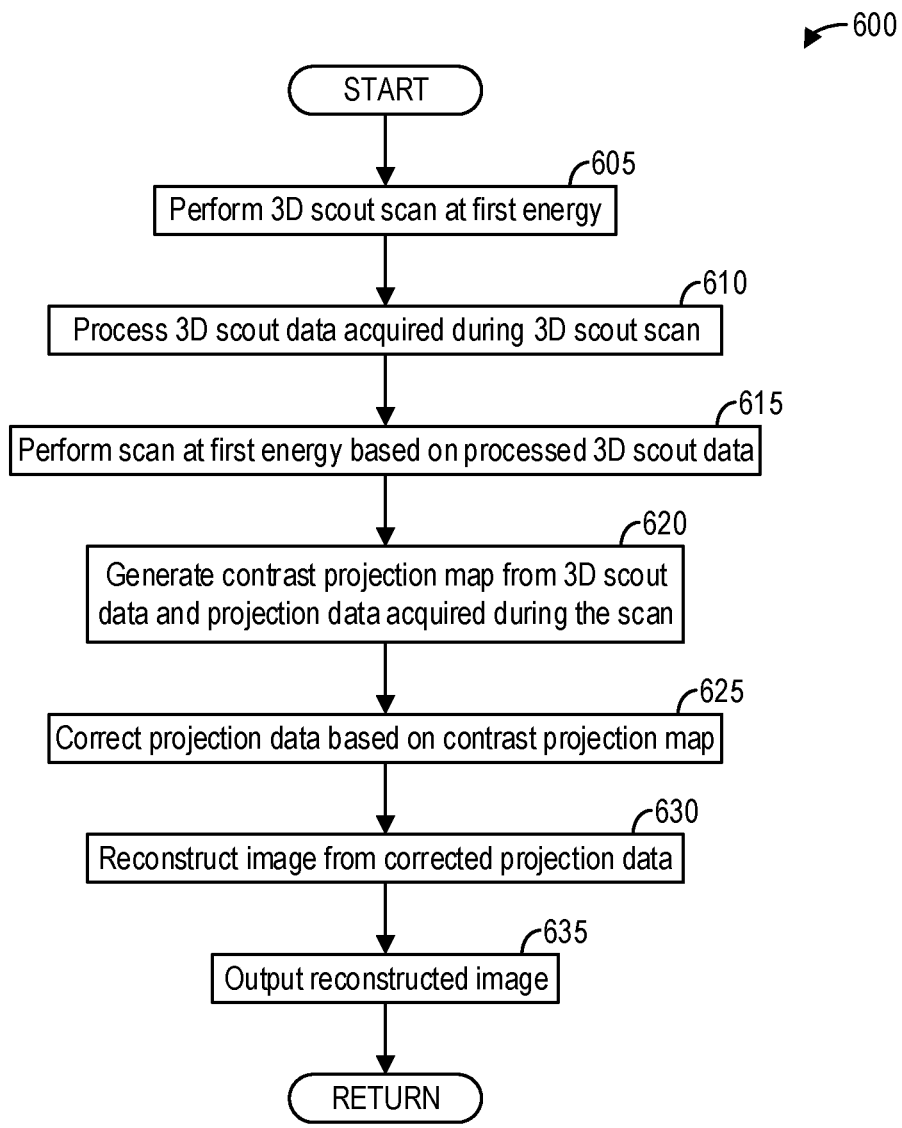
FIG. 6 shows a high-level flow chart illustrating an example method for correcting projection data with 3D scout data acquired at a same energy according to an embodiment.
Figure 7:
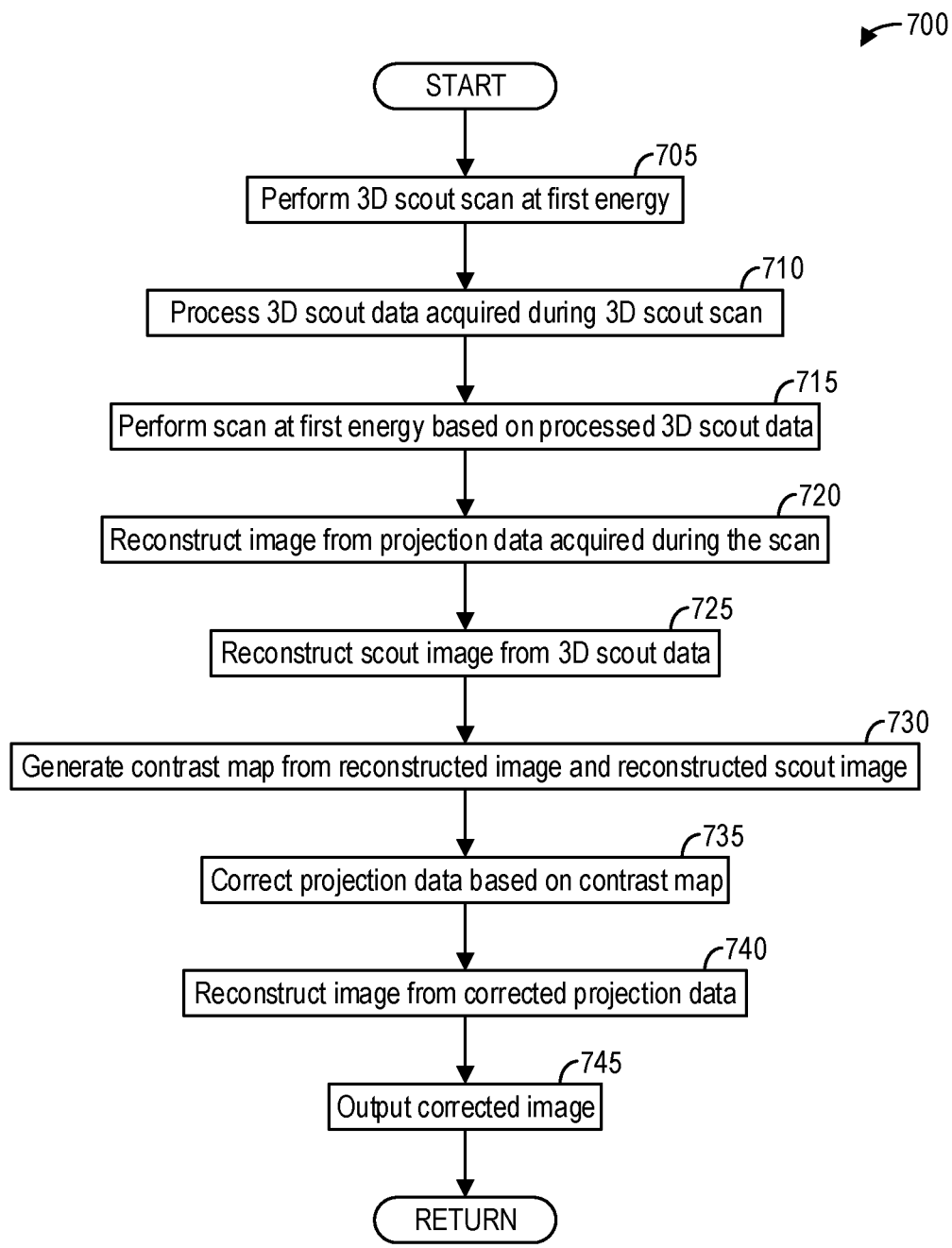
FIG. 7 shows a high-level flow chart illustrating an example method for correcting image data with 3D scout data acquired at a same energy according to an embodiment.

The following description relates to various embodiments of CT imaging. In particular, systems and methods are provided for improving image quality with 3D scout scans. An example of a CT imaging system that may be used to acquire images processed in accordance with the present techniques is provided in FIGS. 1 and 2. A method for improving image quality, such as the method shown in FIG. 3, includes performing a 3D scout scan. The 3D scout scan may be performed at a different energy or energy spectrum than the main diagnostic scan, and the 3D scout projection data thus acquired may be used to perform beam-hardening corrections in the projection domain or the image domain, as shown in FIGS. 4 and 5. In other examples, the 3D scout scan may be performed at the same energy or energy spectrum as the diagnostic scan, and the 3D scout projection data may still be used to perform beam-hardening corrections in the projection domain or the image domain, as shown in FIGS. 6 and 7.

Though a CT system is described by way of example, it should be understood that the present techniques may also be useful when applied to images acquired using other imaging modalities, such as tomosynthesis, cone-beam computed tomography (CBCT), C-arm angiography, and so forth. The present discussion of a CT imaging modality is provided merely as an example of one suitable imaging modality.

Figure 1:
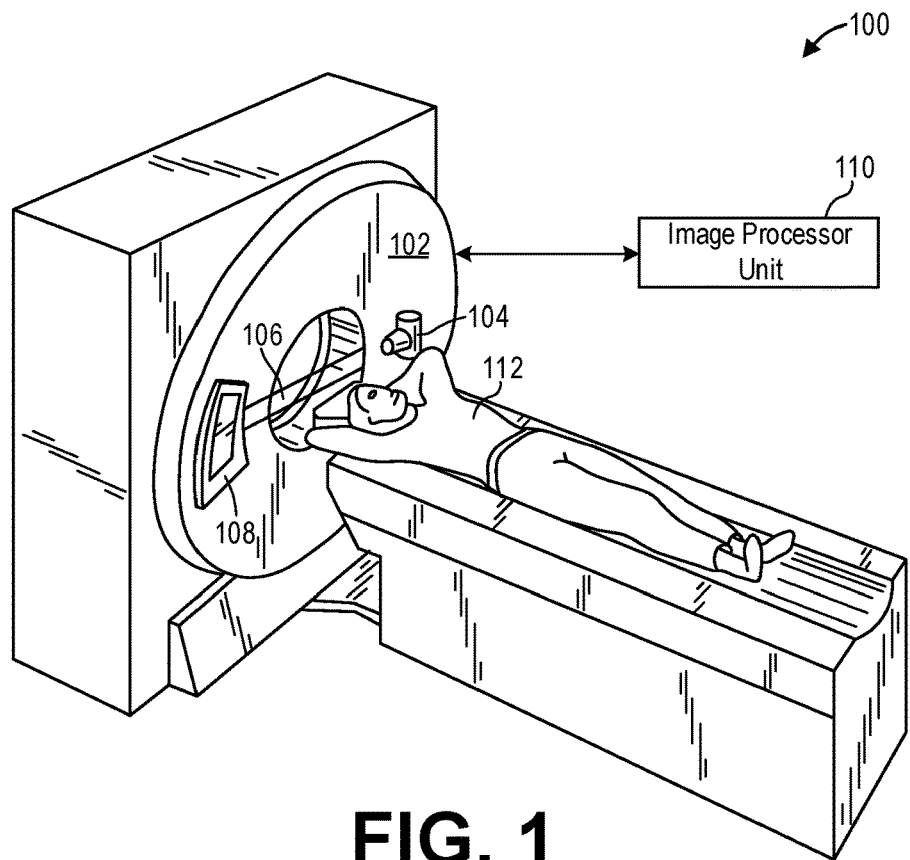
FIG. 1 shows a pictorial view of an imaging system according to an embodiment.

FIG. 1 illustrates an exemplary CT system 100 configured to allow fast and iterative image reconstruction. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the subject 112. Specifically, the x-ray radiation source 104 is configured to project the x-rays 106 towards a detector array 108 positioned on the opposite side of the gantry 102. Although FIG. 1 depicts only a single x-ray radiation source 104, in certain embodiments, multiple x-ray radiation sources may be employed to project a plurality of x-rays 106 for acquiring projection data corresponding to the subject 112 at different energy levels.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered backprojection (FBP) to reconstruct images of a target volume of the patient. As another example, the image processor unit 110 may use an iterative image reconstruction approach such as adaptive statistical iterative reconstruction (ASIR), conjugate gradient (CG), maximum likelihood expectation maximization (MLEM), model-based iterative reconstruction (MBIR), and so on to reconstruct images of a target volume of the subject 112.

In some known CT imaging system configurations, a radiation source projects a fan-shaped beam which is collimated to lie within an X-Y plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

In an axial scan, the projection data is processed to reconstruct an image that corresponds to a two-dimensional slice taken through the object. One method for reconstructing an image from a set of projection data is referred to in the art as the filtered backprojection (FBP) technique. Transmission and emission tomography reconstruction techniques also include statistical iterative methods such as maximum likelihood expectation maximization (MLEM) and ordered-subsets expectation reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a helical scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present disclosure in which data representing an image is generated but a viewable image is not. Therefore, as used herein the term "image" broadly refers to both viewable images and data representing a viewable image. However, many embodiments generate (or are configured to generate) at least one viewable image.

Figure 2:
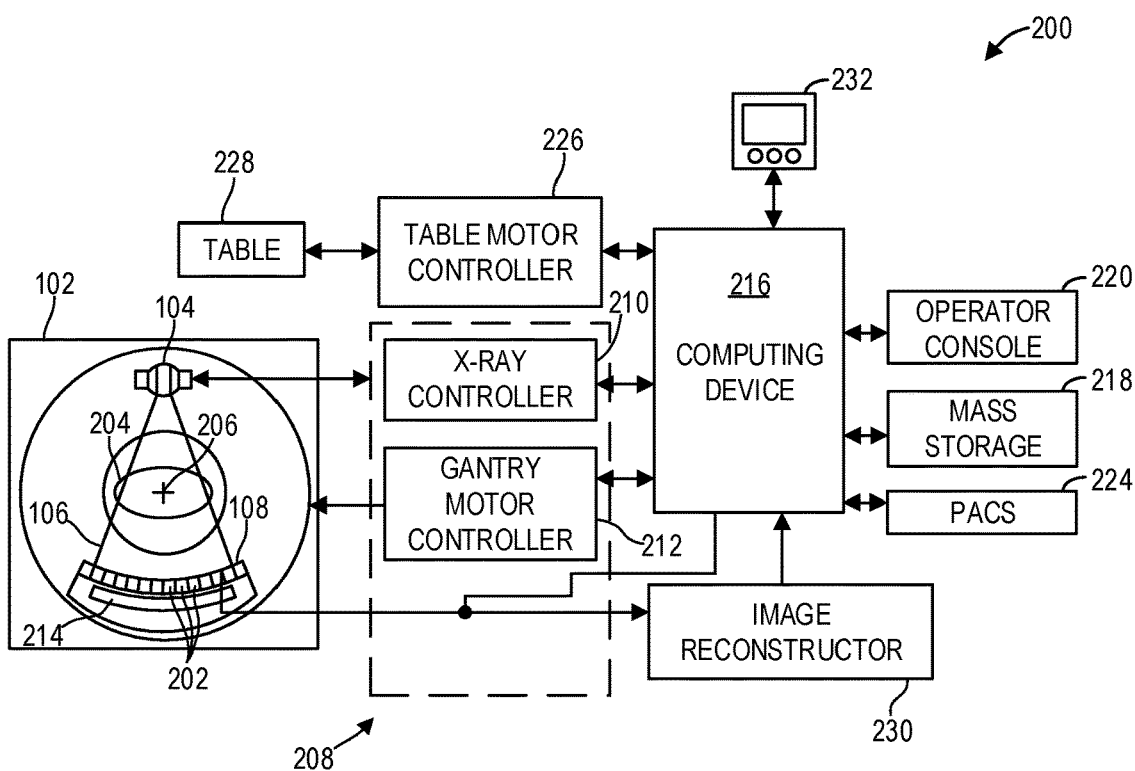
FIG. 2 shows a block schematic diagram of an exemplary imaging system according to an embodiment.

FIG. 2 illustrates an exemplary imaging system 200 similar to the CT system 100 of FIG. 1. In accordance with aspects of the present disclosure, the imaging system 200 is configured to acquire three-dimensional (3D) scout scans and perform beam hardening corrections using data acquired during the 3D scout scan. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray radiation source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In dual or multi-energy imaging, two or more sets of projection data are typically obtained for the imaged object at different tube peak kilovoltage (kVp) levels, which change the peak and spectrum of energy of the incident photons comprising the emitted x-ray beams or, alternatively, at a single tube kVp level or spectrum with an energy resolving detector of the detector array 108.

The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the x-ray radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer or computing device 216. In one example, the computing device 216 stores the data in a storage device such as mass storage 218. The mass storage 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) and/or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more of the functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device or mass storage 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in imaging system 200. For example, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing system 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

The imaging system 200 is configured to perform a 3D scout scan. As an example, the imaging system 200 performs a helical scan with a lower radiation dose than a typical diagnostic scan to acquire 3D scout projection data. In some examples, the imaging system 200 may be configured for sparse view data acquisition and image reconstruction, wherein the x-ray source 104 and the detector array 108 may be configured to acquire data at a reduced number of views compared to a typical scan, thereby reducing a radiation dosage. As one illustrative and non-limiting example, a gating technique may be used to enable the sparse view acquisition. In yet other examples, a combination of a low tube current, a high helical pitch, and a sparse view acquisition may be used to perform the 3D scout scan. Further, it should be appreciated that the 3D scout scan produces 3D scout projection data corresponding to the internal anatomy or contents of the subject being scanned. That is, the 3D scout projection data may be reconstructed into a 3D image volume depicting the internal composition of the subject. In contrast, a conventional scout scan only produces a two-dimensional scout image that is used for planning a full 3D diagnostic scan. As described further herein, in addition to using the 3D scout projection data to plan a diagnostic scan, the imaging system 200 is configured to use the 3D scout projection data for corrections to projection data and/or image data acquired during the diagnostic scan.

Figure 3:
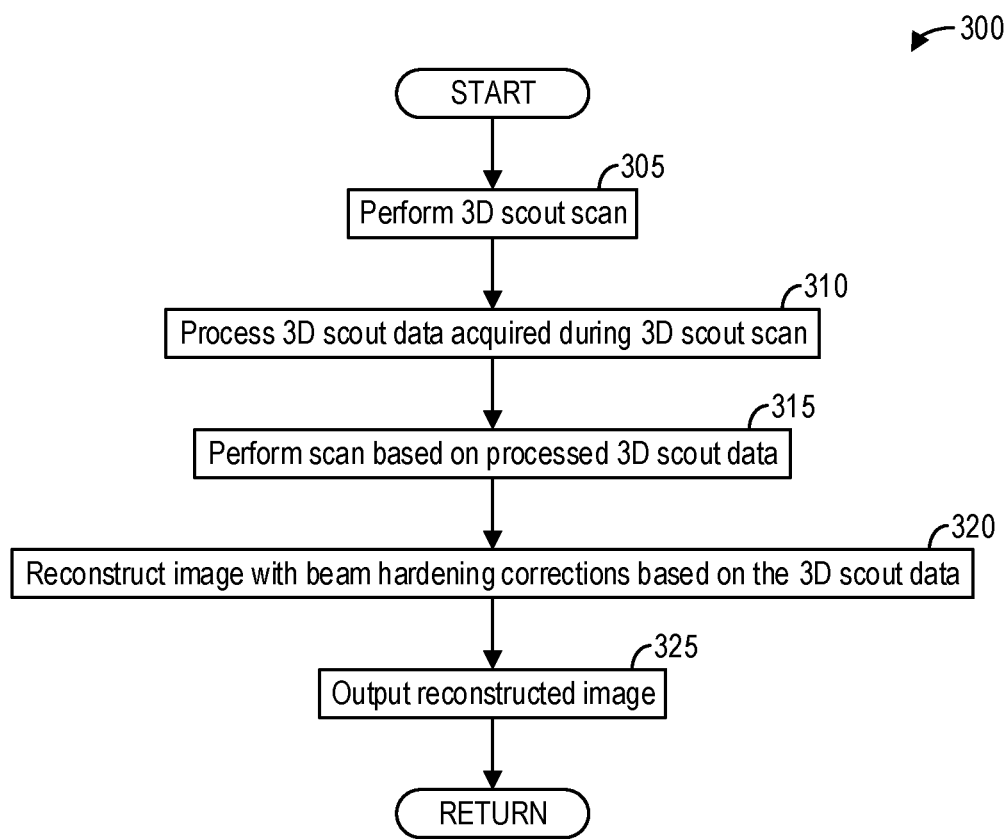
FIG. 3 shows a high-level flow chart illustrating an example method for image reconstruction with 3D scout data according to an embodiment.

FIG. 3 shows a high-level flow chart illustrating an example method 300 for image reconstruction with 3D scout data according to an embodiment. In particular, method 300 relates to using data acquired during a 3D scout scan to correct data acquired during a full scan. Method 300 is described with regard to the systems and components depicted in FIGS. 1 and 2, though it should be appreciated that the method may be implemented with other systems and/or components without departing from the scope of the present disclosure. Method 300 may be implemented as executable instructions in non-transitory memory of a computing device, such as computing device 216 and/or image reconstructor 230.

Method 300 begins at 305. At 305, method 300 performs a 3D scout scan. To perform the 3D scout scan, the subject to be scanned, such as a patient, may be positioned within the imaging space of the imaging system. To that end, the method may control the table, for example via the table motor controller, to move such that the region of interest to be imaged is within the bore of the gantry. The imaging system is then controlled to acquire scout projection data with a reduced radiation dosage with respect to a typical diagnostic scan. In some examples, the scout scan is performed with a lower tube current and a higher helical pitch relative to a typical diagnostic scan. For example, during the scout scan, the subject is moved (e.g., by moving the table 228 with the table motor controller 226) through the gantry bore while the x-ray source is controlled to generate a low-dose x-ray beam. For a higher helical pitch, one or more of the speed of the table movement and the rotational speed of the x-ray source around the gantry bore is increased relative to a normal scan.

Additionally or alternatively, in other examples, the imaging system may be configured for sparse view data acquisition and image reconstruction, wherein the x-ray source and the detector array may be configured to acquire data at a reduced number of views compared to a typical scan, thereby reducing a radiation dosage. As one illustrative and non-limiting example, a gating technique may be used to enable the sparse view acquisition. In yet other examples, a combination of a low tube current, a high helical pitch, and a sparse view acquisition may be used to perform the scout scan.

Further, it should be appreciated that the 3D scout scan produces 3D scout projection data corresponding to the internal anatomy or contents of the subject being scanned. That is, the 3D scout projection data may be reconstructed into a 3D image volume depicting the internal composition of the subject. In contrast, a conventional scout scan only produces a two-dimensional scout image that is used for planning a full 3D diagnostic scan.

In some examples, the 3D scout scan may be performed at a different energy level relative to the main scan. For example, the 3D scout scan may be performed at a first energy spectrum, while the main scan may be performed at a second energy spectrum different from the first energy spectrum. Since the scout scan and the main scan are performed at different energy levels, the method may apply dual-energy techniques such as material decomposition or characterization to the projection data acquired during the scout scan and the main scan. As discussed further herein, such techniques allow the method to correct projection data acquired during the main scan, thereby resulting in improved image quality. Methods for using scout data acquired at a different energy level are described further herein with regard to FIGS. 4 and 5.

In other examples, the 3D scout scan may be performed at the same energy level or spectrum as the main scan. As described further herein, the 3D scout data acquired at the same energy spectrum as the projection data acquired during the main scan may be used to correct the projection data, especially when the main scan is contrast-enhanced. Methods for using scout data acquired at a same energy level as the main scan are described further herein with regard to FIGS. 6 and 7.

Referring again to FIG. 3, method 300 continues to 310 after performing the 3D scout scan. At 310, method 300 processes 3D scout data acquired during the 3D scout scan. In particular, the method processes the 3D scout data to determine one or more parameters for the full scan.

As one example, the 3D scout data may be processed to automatically or manually localize patient anatomy in the 3D scout image. For example, the method may reconstruct a 3D scout image from the 3D scout data, register a pre-labeled 3D volumetric atlas to the 3D scout image, and transform a segmentation and/or anatomical labels from the atlas to the 3D scout image. The method may use the localized patient anatomy information for dose management to individual structures, determining the scan range, automated optimization of reconstruction parameters, determining patient orientation within the gantry, and so on.

As another example, the 3D scout data may be processed to automatically determine an automated exposure control (AEC) protocol that specifies exposure parameters (e.g., peak kilovoltage and milliampere second values) that define the x-ray beam generated by the x-ray source for the full scan. For example, the method may determine a tube current that optimally adapts to the subject based on varying amounts of attenuation in different views of the subject as determined by the 3D scout data.

At 315, method 300 performs a scan based on the processed 3D scout data. The scan comprises a full diagnostic scan with an increased dose relative to the scout scan. To perform the scan based on the processed 3D scout data, the method performs the scan based on the patient localization determined with the 3D scout data. Further, the method performs the scan using the AEC protocol determined based on the 3D scout data.

After performing the scan at 315, method 300 continues to 320. At 320, method 300 reconstructs an image with beam-hardening corrections based on the 3D scout data. Generally, method 300 uses the 3D scout data to improve the image quality of the image reconstructed from projection data acquired during the scan at 315.

More specifically, in some examples, the method corrects the projection data acquired during the scan based on the 3D scout data prior to image reconstruction, such that the corrections are performed in the projection domain. Methods for performing beam-hardening corrections in the projection domain based on the 3D scout data are described further herein with regard to FIGS. 4 and 6.

In other examples, the method performs the beam-hardening corrections in the image domain rather than the projection domain. For example, the method may reconstruct a 3D scout image from the 3D scout data as well as an image from the projection data acquired during the scan, and then may perform corrections using the 3D scout image and the image. Methods for performing beam-hardening corrections in the image domain based on the 3D scout data are described further herein with regard to FIGS. 5 and 7.

Further, in examples wherein the scout scan is performed at a different energy spectrum than the main scan, the corrections may be performed using dual-energy techniques such as material decomposition. Such examples are described further herein with regard to FIGS. 4 and 5. In examples wherein the scout scan is performed at the same energy spectrum as the main scan, the corrections may be obtained based on a contrast map determined from the scout scan and the main scan. Such examples are described further herein with regard to FIGS. 6 and 7.

At 325, method 300 outputs the reconstructed image. For example, the method may output to reconstructed image to one or more of a display 232 for display to a user, mass storage 218 for later retrieval and review, PACS 224 for storage and/or review at another workstation, and so on. Method 300 then ends.

Thus, a method for improving image quality is provided that includes reconstructing an image from projection data acquired during a diagnostic scan of a patient with corrections based on scout projection data acquired during a 3D scout scan of the patient.

FIG. 4 shows a high-level flow chart illustrating an example method 400 for correcting projection data with 3D scout data acquired at a different energy according to an embodiment. In particular, method 400 relates to performing corrections in the projection domain using 3D scout data acquired at a different energy spectrum. Method 400 is described with regard to the systems and components depicted in FIGS. 1 and 2, though it should be appreciated that the method may be implemented with other systems and/or components without departing from the scope of the present disclosure. Method 400 may be implemented as executable instructions in non-transitory memory of a computing device, such as computing device 216 and/or image reconstructor 230.

Method 400 begins at 405. At 405, method 400 performs a 3D scout scan at a first energy. Method 400 may perform the 3D scout scan as described hereinabove with regard to FIG. 3. Continuing at 410, method 400 processes the 3D scout data acquired during the 3D scout scan. In particular, method 400 processes the 3D scout data acquired during the 3D scout scan to determine one or more parameters for the diagnostic scan. For example, as discussed hereinabove with regard to FIG. 3, method 400 may process the 3D scout data to automatically localize patient anatomy in the 3D scout image. Further, method 400 may process the 3D scout data to automatically determine an AEC protocol that specifies exposure parameters that define the x-ray beam generated by the x-ray source for the full scan.

At 415, method 400 performs a scan at a second energy based on the processed 3D scout data, the second energy different from the first energy. As an illustrative and non-limiting example, the first energy may comprise 80 kV while the second energy may comprise 120 kV, such that the 3D scout scan is performed at 80 kV while the scan is performed at 120 kV. It should be appreciated that in some examples, the terms "first energy" and "second energy" may refer to different ranges of an energy spectrum, such as a first energy spectrum and a second energy spectrum, while in other examples, the terms "first energy" and "second energy" refer to specific energy levels. The scan comprises a full diagnostic scan with an increased dose relative to the scout scan. To perform the scan based on the processed 3D scout data, method 400 performs the scan based on the patient localization determined with the 3D scout data. Further, method 400 performs the scan using the AEC protocol determined based on the 3D scout data.

After performing the scan at the second energy, method 400 continues to 420. At 420, method 400 corrects projection data acquired during the scan based on the 3D scout data. For simplicity, the projection data acquired during the scan at 415 is hereinafter referred to as the main projection data while the 3D scout data acquired during the 3D scout scan at 405 is referred to as the scout projection data. Since the main projection data and the scout projection data are acquired at different energy spectra, the main projection data and the scout projection data can be mixed together to perform material decomposition (MD). However, since the scout projection data is acquired at low-flux conditions, method 400 may optionally de-noise the scout projection data prior to performing MD.

As an illustrative and non-limiting example, method 400 may determine beam-hardening corrections to the main projection data by expressing the main projection data and the scout projection data respectively as:

$$p_1 = \frac{\int S_1(E) \cdot \eta_1(E) \cdot \exp\left(-\left(\frac{\mu}{\rho}\right)_w(E) \cdot \delta_w - \left(\frac{\mu}{\rho}\right)_b(E) \cdot \delta_b\right) \cdot E \, dE}{\int S_1(E) \cdot \eta_1(E) \cdot E \, dE},$$

$$p_2 = \frac{\int S_2(E) \cdot \eta_2(E) \cdot \exp\left(-\left(\frac{\mu}{\rho}\right)_w(E) \cdot \delta_w - \left(\frac{\mu}{\rho}\right)_b(E) \cdot \delta_b\right) \cdot E \, dE}{\int S_2(E) \cdot \eta_2(E) \cdot E \, dE},$$

where $S_1(E)$ and $S_2(E)$ are tube spectrum after intrinsic filter and bowtie filter at two different energy levels, $\eta_1(E)$ and $\eta_2(E)$ are detector efficiency at two different energy levels, and $(\mu/\rho)_w$, and $(\mu/\rho)_b$ are mass attenuation coefficients of water and bone, respectively. Further, $\delta_w$ and $\delta_b$ are the area densities of water and bone, respectively:

$$\delta_w = \int \rho_w(\vec{r}) \, dl,$$

$$\delta_b = \int \rho_b(\vec{r}) \, dl.$$

For non-contrast scans, the dual energy information from the scout scan and the main scan can be used to generate $\delta_w$ and $\delta_b$ (i.e., the line integral of the bone and water density) using 2D lookup tables or a 2D polynomial fitting:

$$\delta_b = \sum_{i,j} a_{i,j} \cdot p_1^i \cdot p_2^j,$$

$$\delta_w = \sum_{i,j} b_{i,j} \cdot p_1^i \cdot p_2^j,$$

where $a_{i,j}$ and $b_{i,j}$ are beam-hardening coefficients. The corrected projection $p_{corr}$ is the monochromatic projection at a given energy $E_0$:

$$p_{corr} = \left(\frac{\mu}{\rho}\right)_w (E_0) \cdot \delta_w + \left(\frac{\mu}{\rho}\right)_b (E_0) \cdot \delta_b$$

Another approach to obtaining the beam-hardening-corrected projection data $p_{corr}$ is to calculate the correction term from $\delta_b$ and the main projection data (assuming the main projection data comprises $p_1$ here without loss of generality):

$$\Delta p = \sum_{i,j} c_{i,j} \cdot \delta_b^i \cdot p_1^j,$$

$$p_{corr} = p_1 + \Delta p,$$

where $\Delta p$ comprises the beam-hardening correction.

After correcting the main projection data to obtain corrected projection data, method 400 continues to 425. At 425, method 400 reconstructs an image from the corrected projection data. Method 400 may reconstruct the image by applying an analytic or iterative image reconstruction algorithm to the corrected projection data. At 430, method 400 outputs the reconstructed image. For example, method 400 may output the reconstructed image to one or more of a display device such as display 232, a storage device such as mass storage 218, and a picture archiving and communication system such as PACS 224. Method 400 then ends.

Thus, a method comprises acquiring scout projection data and main projection data at different energy spectra, combining the scout projection data and the main projection data in the projection domain to obtain beam-hardening-corrected projection data, and reconstructing an image from the beam-hardening-corrected projection data.

In another example, the beam-hardening corrections may be obtained in the image domain rather than the projection domain. FIG. 5 shows a high-level flow chart illustrating an example method 500 for correcting image data with 3D scout data acquired at a different energy according to an embodiment. Method 500 is described with regard to the systems and components depicted in FIGS. 1 and 2, though it should be appreciated that the method may be implemented with other systems and/or components without departing from the scope of the present disclosure. Method 500 may be implemented as executable instructions in non-transitory memory of a computing device, such as computing device 216 and/or image reconstructor 230.

Method 500 begins at 505. At 505, method 500 performs a 3D scout scan at a first energy, as described hereinabove with regard to FIGS. 3 and 4. Similarly, at 510, method 500 processes the 3D scout data acquired during the 3D scout scan to perform patient anatomy localization and to determine an AEC protocol. At 515, method 500 performs a diagnostic scan at a second energy based on the processed 3D scout data, for example based on the patient anatomy localization and the AEC protocol.

At 520, method 500 reconstructs an image from projection data acquired during the scan. At 525, method 500 reconstructs a scout image from the 3D scout data. Method 500 may use a suitable analytic or iterative image reconstruction algorithm to reconstruct the image and the scout image.

At 530, method 500 corrects the reconstructed image based on the reconstructed scout image. As a non-limiting example, method 500 uses the reconstructed scout image to obtain beam-hardening corrections for the reconstructed image.

Conventionally, the second-order beam hardening correction for bone is implemented by first segmenting the bone voxels by global thresholding to create a bone mask. The bone voxels within the mask are then forward projected to generate the line integral of the bone voxels. The correction term $\Delta p$ can be modeled by 2D polynomial fitting:

$$\Delta p = \sum_{i,j} a_{i,j} \cdot p_{bone}^i \cdot p_{total}^j.$$

The challenge is that the bone voxels are not accurate due to the beam hardening. Thus, the correction is in iterative fashion, which affects the computational efficiency. Moreover, in the contrast-enhanced cases the HU values of bone and iodine voxels are often overlapped and difficult to segment.

Method 500 mitigates this issue by introducing new information of the scout scan at a different energy. As an illustrative and non-limiting example, if the reconstructed voxel has the CT number of $x_1$ at one energy and $x_2$ at another energy, the decomposed water and bone results are $$\begin{bmatrix} x_b \\ x_w \end{bmatrix} = \begin{bmatrix} \left(\frac{\mu}{\rho}\right)_b (E_1) & \left(\frac{\mu}{\rho}\right)_w (E_1) \\ \left(\frac{\mu}{\rho}\right)_b (E_2) & \left(\frac{\mu}{\rho}\right)_w (E_2) \end{bmatrix}^{-1} \begin{bmatrix} x_1 \\ x_2 \end{bmatrix}.$$

The decomposed bone voxels are less sensitive to the beam hardening in the first pass reconstruction if the effective energy levels $E_1$ and $E_2$ are properly tuned. A thresholding to the $x_b$ result can be used to segment the iodine voxels if the main scan is a contrast-enhanced scan. The forward projection of the bone voxels leads to the line integration of the bone voxels:

$$\delta_b = \int x_b dl.$$

Then a technique similar to the projection-based approach described hereinabove with regard to FIG. 4 may be used to obtain the corrected image $p_{corr}$:

$$\Delta p = \sum_{i,j} c_{i,j} \cdot \delta_b^i \cdot p_1^j,$$

$$p_{corr} = x_1 + \Delta x,$$

where $x_1$ and $\Delta x$ are the reconstructions of $p_1$ and $\Delta p$, respectively.

At 535, method 500 outputs the corrected image. For example, method 500 may output the corrected image to one or more of a display device such as display 232, a storage device such as mass storage 218, and a picture archiving and communication system such as PACS 224. Method 500 then ends.

Thus, a method comprises acquiring scout projection data and main projection data at different energies, reconstructing a scout image and an image from the scout projection data and the main projection data respectively, determining beam-hardening corrections to the image based on the scout image, and correcting the image with the beam-hardening corrections.

In some examples, second-order beam-hardening corrections can be applied by performing a multi-material correction. For example, for a given x-ray path, the total attenuation in the main scan may be written as:

$$p_{total} = \frac{\int S(E) \cdot \eta(E) \cdot \exp\left(-\sum_i \mu_i(E) L_i\right) \cdot E \, dE}{\int S(E) \cdot \eta(E) \cdot E \, dE},$$

where S(E) is the tube spectrum after intrinsic filter and bowtie filter, η(E) is the detector efficiency, $\mu_i$ and $L_i$ are the attenuation coefficient and path length of the $i^{th}$ material. For a typical clinical case, the materials may be selected as water, iodine, and bone. For a scintillator-based detector, the detected intensity is weighted by the energy E. To perform a second-order beam-hardening correction by performing a multi-material correction, a first pass reconstruction of $p_{total}$ is segmented, converted to two basis materials (e.g., water and iodine), and forward projected to generate the projection of the basis materials $p_w$ and $p_{io}$. The monochromatic projection data is the linear combination of the two basis materials:

$$p_{mono} = \mu_w(E_0)L_w + \mu_{io}(E_0)L_{io},$$

where $E_0$ is a predefined effective energy. The correction term for the second-order beam-hardening correction is calculated by building a 2D polynomial model:

$$\Delta p = \sum_{i,j} a_{i,j} \cdot p_{total}^i \cdot p_{io}^j.$$

The correction term Δp is defined as the difference between the ideal value $p_{mono}$ and the total attenuation $p_{total}$. Thus, the corrected projection is:

$$p_{corrected} = p_{total} + \Delta p.$$

However, segmenting the first-pass reconstruction of $p_{total}$ to differentiate into different basis materials is difficult because only one energy level is available. For example, mis-segmentation is likely unavoidable because the CT numbers of different materials such as contrast-enhanced blood vessels and bones are overlapped. The methods described herein below with regard to FIGS. 6 and 7 enable more accurate beam-hardening corrections by using 3D scout data to improve the segmentation step.

For example, FIG. 6 shows a high-level flow chart illustrating an example method 600 for correcting projection data with 3D scout data acquired at a same energy according to an embodiment. Method 600 is described with regard to the systems and components depicted in FIGS. 1 and 2, though it should be appreciated that the method may be implemented with other systems and/or components without departing from the scope of the present disclosure. Method 600 may be implemented as executable instructions in non-transitory memory of a computing device, such as computing device 216 and/or image reconstructor 230.

Method 600 begins at 605. At 605, method 600 performs a 3D scout scan at a first energy. Method 600 performs the 3D scout scan as described hereinabove with regard to FIG. 3. Continuing at 610, method 600 processes the 3D scout data acquired during the 3D scout scan. For example, method 600 may process the 3D scout data as described hereinabove to perform patient anatomy localization and to determine an AEC protocol. At 615, method 600 performs a diagnostic scan at the first energy based on the processed 3D scout data. That is, method 600 performs the 3D scout scan and the diagnostic scan at the same energy. As a non-limiting example, method 600 uses the patient anatomy localization and the AEC protocol determined at 610 to perform the diagnostic scan.

At 620, method 600 generates a contrast projection map from the 3D scout data and projection data acquired during the scan. The contrast projection map comprises the projection of the distribution of a contrast agent during the main scan. For example, since the 3D scout scan is not contrast enhanced but the main diagnostic scan is contrast-enhanced, if the contrast agent comprises iodine, method 600 determines the projection of the distribution of iodine by subtracting the 3D scout data from the projection data.

Continuing at 625, method 600 corrects the projection data based on the contrast projection map. Instead of performing global thresholding to segment the iodine as mentioned above, the contrast projection map generated at 620 already comprises the iodine distribution in projection space. Thus, to correct the projection data acquired at 615, method 600 subtracts the contrast projection map from the projection data collected at 615, performs a first-pass reconstruction with the resulting projection data, and segments the bone voxels from soft tissue. This segmentation is straightforward since the contrast agent has been subtracted. Method 600 converts the bone voxels to basis material (e.g., water and iodine) maps and forward projects the converted iodine maps. The iodine equivalent projections are obtained by combining the contrast projection map generated at 620 and the forward projection of the converted iodine map from bone voxels. Thus, method 600 performs multi-material correction as discussed above with the iodine equivalent projections. Method 600 therefore obtains beam-hardening corrections to the main projection data without residual artifacts typically caused by determining iodine equivalent projections from forward projection of a re-mapped volume.

At 630, method 600 reconstructs an image from the corrected projection data. Method 600 reconstructs the image by applying an analytic or iterative image reconstruction algorithm to the corrected projection data. Continuing at 635, method 600 outputs the reconstructed image to one or more of a display device such as display 232, a storage device such as mass storage 218, and a PACS such as PACS 224. Method 600 then ends.

Thus, a method for reducing or minimizing beam-hardening artifacts for images acquired at a single energy rather than a dual energy is provided. While method 600 relates to determining the iodine distribution in projection space, it should be appreciated that the iodine distribution may also be obtained in image space. For example, FIG. 7 shows a high-level flow chart illustrating an example method 700 for correcting image data with 3D scout data acquired at a same energy according to an embodiment. Method 700 is described with regard to the systems and components depicted in FIGS. 1 and 2, though it should be appreciated that the method may be implemented with other systems and/or components without departing from the scope of the present disclosure. Method 700 may be implemented as executable instructions in non-transitory memory of a computing device, such as computing device 216 and/or image reconstructor 230.

Method 700 begins at 705. At 705, method 700 performs a 3D scout scan at a first energy. Method 600 performs the 3D scout scan as described hereinabove with regard to FIG. 3. Continuing at 710, method 700 processes the 3D scout data acquired during the 3D scout scan. For example, method 700 processes the 3D scout data as described hereinabove to perform patient anatomy localization and to determine an AEC protocol. At 715, method 700 performs a scan at the first energy based on the processed 3D scout data. For example, method 700 uses the patient anatomy localization and the AEC protocol determined at 710 to perform the diagnostic scan.

Continuing at 720, method 700 reconstructs an-image from projection data acquired during the scan at 715. At 725, method 700 reconstructs a scout image from the 3D scout data. Method 700 reconstructs the image and the scout image with an analytic or an iterative image reconstruction algorithm.

At 730, method 700 generates a contrast map from the reconstructed image and the reconstructed scout image. For example, method 700 subtracts the reconstructed scout image from the reconstructed image. Since the reconstructed scout image is not contrast-enhanced while the reconstructed image is contrast-enhanced, the difference image or contrast map comprises an image depicting the distribution of contrast.

At 735, method 700 corrects the projection data based on the contrast map. To correct the projection data based on the contrast map, method 700 first subtracts the contrast map from the reconstructed image generated at 720, and then segments the bone voxels from soft tissue with global thresholding. This segmentation is straightforward because the contrast agent has been removed from the image. It is well known that the attenuation of bone can be converted to the linear combination of the attenuation of water and iodine which are defined as "basis materials":

$$\mu_b w_1 \mu_w + w_2 \mu_{io},$$

where $\mu_b$ is the attenuation coefficient for bone, $\mu_w$ is the attenuation coefficient for water, $\mu_{io}$ is the attenuation coefficient for iodine, and $w_1$ and $w_2$ are weights. Thus, the segmented bone voxels can be converted to water and iodine maps. The total iodine map is the sum of the contrast map generated at 730 and the converted iodine map from the bone voxels. Method 700 obtains the iodine equivalent projections by forward projecting the total iodine map, and then performs multi-material corrections with the iodine equivalent projections to obtain the beam-hardening correction to the projection data as described hereinabove with regard to FIG. 6.

At 740, method 700 reconstructs an image from the corrected projection data. Method 700 reconstructs the image with an analytic or an iterative image reconstruction algorithm. Continuing at 745, method 700 outputs the corrected image to one or more of a display device such as display 232, a storage device such as mass storage 218, or a PACS such as PACS 224. Method 700 then ends.

A technical effect of the disclosure is the acquisition of three-dimensional scout projection data with a three-dimensional scout scan. Another technical effect of the disclosure is the correction of diagnostic projection data with three-dimensional scout data. Yet another technical effect of the disclosure is the acquisition of scout data and the acquisition of projection data at different energies. Another technical effect of the disclosure is a reduction of image artifacts for single energy computed tomography.

In one embodiment, a method comprises reconstructing an image from projection data acquired during a diagnostic scan of a patient with corrections based on scout projection data acquired during a three-dimensional (3D) scout scan of the patient.

In a first example of the method, the method further comprises performing one or more of patient anatomy localization and automatic exposure control for the diagnostic scan based on one or more of the scout projection data and a scout image reconstructed from the scout projection data. In a second example of the method optionally including the first example, the method further comprises performing the 3D scout scan at a first energy and performing the diagnostic scan at a second energy different from the first energy. In a third example of the method optionally including one or more of the first and second examples, reconstructing the image from the projection data with the corrections based on the scout projection data comprises performing beam-hardening reduction on the projection data with the scout projection data to obtain corrected projection data, and reconstructing the corrected projection data into the image. In a fourth example of the method optionally including one or more of the first through third examples, reconstructing the image from the projection data with the corrections based on the scout projection data comprises reconstructing a scout image from the scout projection data, reconstructing an uncorrected image from the projection data, and performing beam-hardening reduction on the uncorrected image with the scout image to obtain a corrected image, wherein the image comprises the corrected image. In a fifth example of the method optionally including one or more of the first through fourth examples, the method further comprises performing the 3D scout scan at a specified energy, and performing the diagnostic scan at the specified energy. In a sixth example of the method optionally including one or more of the first through fifth examples, reconstructing the image from the projection data with the corrections based on the scout projection data comprises obtaining a distribution of contrast in the patient, calculating beam-hardening corrections based on the distribution of contrast, and reconstructing the image from the projection data with the beam-hardening corrections. In a seventh example of the method optionally including one or more of the first through sixth examples, obtaining the distribution of contrast in the patient comprises subtracting the scout projection data from the projection data. In an eighth example of the method optionally including one or more of the first through seventh examples, obtaining the distribution of contrast in the patient comprises reconstructing a scout image from the scout projection data, reconstructing an uncorrected image from the projection data, and subtracting the scout image from the uncorrected image.

In another embodiment, a method comprises performing a 3D scout scan of a patient to acquire 3D scout projection data, performing a diagnostic scan of the patient to acquire projection data, and reconstructing an image from the projection data with beam-hardening corrections based on the 3D scout projection data.

In a first example of the method, the diagnostic scan is contrast-enhanced with a contrast agent, and reconstructing the image from the projection data with the beam-hardening corrections based on the 3D scout projection data comprises obtaining a distribution of the contrast agent in the patient, calculating beam-hardening corrections based on the distribution of the contrast agent, and reconstructing the image from the projection data with the beam-hardening corrections. In a second example of the method optionally including the first example, obtaining the distribution of contrast in the patient comprises one of subtracting the scout projection data from the projection data or reconstructing a scout image from the scout projection data, reconstructing an uncorrected image from the projection data, and subtracting the scout image from the uncorrected image. In a third example of the method optionally including one or more of the first and second examples, the method further comprises performing the 3D scout scan at a first energy and performing the diagnostic scan at a second energy different from the first energy. In a fourth example of the method optionally including one or more of the first through third examples, reconstructing the image from the projection data with the beam-hardening corrections based on the 3D scout projection data comprises performing beam-hardening reduction on the projection data with the 3D scout projection data to obtain corrected projection data, and reconstructing the corrected projection data into the image. In a fifth example of the method optionally including one or more of the first through fourth examples, reconstructing the image from the projection data with the beam-hardening corrections based on the 3D scout projection data comprises reconstructing a scout image from the 3D scout projection data, reconstructing an uncorrected image from the projection data, and performing beam-hardening reduction on the uncorrected image with the scout image to obtain a corrected image, wherein the image comprises the corrected image.

In yet another embodiment, a system comprises an x-ray source that emits a beam of x-rays towards a subject to be imaged, a detector that receives the x-rays attenuated by the subject, a data acquisition system (DAS) operably connected to the detector, and a computing device operably connected to the DAS and configured with executable instructions in non-transitory memory that when executed cause the computing device to reconstruct an image from projection data acquired, via the DAS, during a diagnostic scan of the subject with corrections based on scout projection data acquired, via the DAS, during a 3D scout scan of the subject.

In a first example of the system, the x-ray source and the detector are controlled to acquire the scout projection data at a first energy and the projection data at a second energy different from the first energy. In a second example of the system optionally including the first example, the computing device is further configured with executable instructions in non-transitory memory that when executed cause the computing device to correct the projection data with the scout projection data for beam-hardening artifacts, wherein the correction is performed in image space or projection space. In a third example of the system optionally including one or more of the first and second examples, the x-ray source and the detector are controlled to acquire the scout projection data and the projection data at a same energy. In a fourth example of the system optionally including one or more of the first through third examples, the diagnostic scan is enhanced with a contrast agent, and the computing device is further configured with executable instructions in non-transitory memory that when executed cause the computing device to calculate a distribution of the contrast agent in the subject based on the scout projection data and the projection data, and calculate the corrections based on the distribution of the contrast agent.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    performing a three-dimensional (3D) scout imaging scan of a patient at a first energy to acquire 3D scout projection image data;
    performing a diagnostic imaging scan of the patient at a second energy different from the first energy to acquire diagnostic projection image data;
    perform a beam-hardening reduction on the diagnostic projection data by combining the 3D scout projection image data with the diagnostic projection image data for a material decomposition to generate a beam-hardening corrected diagnostic projection image data;
    reconstructing an image from the beam-hardening corrected diagnostic projection image data to obtain a beam-hardening corrected diagnostic image.

2. The method of claim 1, further comprising performing one or more of a patient anatomy localization and an automatic exposure control for the diagnostic imaging scan based on one or more of the 3D scout projection image data and a 3D scout image reconstructed from the 3D scout projection image data.

3. A method, comprising:
    performing a three-dimensional (3D) scout imaging scan of a patient at a first energy to acquire 3D scout projection image data;
    reconstructing a scout image from the 3D scout projection image data;
    performing a diagnostic imaging scan of the patient at a second energy different from the first energy to acquire diagnostic projection image data;
    reconstructing a diagnostic image from the diagnostic projection image data;
    obtaining a beam-hardening correction using the reconstructed scout image
    performing a beam-hardening reduction on the reconstructed diagnostic image with the obtained beam-hardening correction for a material decomposition to obtain a beam-hardening corrected diagnostic image.

4. A system, comprising:
    an x-ray source that emits a beam of x-rays towards a subject to be imaged;
    a detector that receives the beam of x-rays attenuated by the subject;
    a data acquisition system (DAS) operably connected to the detector; and
    a computing device operably connected to the DAS comprising a non-transitory memory having stored thereupon executable instructions that when executed cause the computing device to:
        perform a beam-hardening correction on first projection data to acquire corrected projection data;
        wherein the first projection data is acquired via the DAS during a diagnostic scan of the subject; and
        wherein the beam-hardening correction is performed by combining second projection data acquired via the DAS during a three-dimensional (3D) scout scan with the first projection data acquired during the diagnostic scan for a material decomposition to obtain a beam-hardening corrected projection data;

reconstruct an image from the beam-hardened corrected projection data to obtain a beam-hardening corrected image.

5. The system of claim 4, wherein the x-ray source and the detector are controlled to acquire the scout projection data at a first energy and the projection data at a second energy different from the first energy.

* * * * *